United States Patent
Chang

(10) Patent No.: US 9,983,118 B1
(45) Date of Patent: May 29, 2018

(54) WAFER HOLDING APPARATUS

(71) Applicant: HIMAX TECHNOLOGIES LIMITED, Tainan (TW)

(72) Inventor: Jui-Tang Chang, Tainan (TW)

(73) Assignee: HIMAX TECHNOLOGIES LIMITED, Tainan (TW)

( * ) Notice: Subject to any disclaimer, the term of this patent is extended or adjusted under 35 U.S.C. 154(b) by 0 days. days.

(21) Appl. No.: 15/613,139

(22) Filed: Jun. 3, 2017

(51) Int. Cl.
| | | |
|---|---|---|
| *G01N 21/00* | (2006.01) | |
| *H01L 21/00* | (2006.01) | |
| *G01N 21/01* | (2006.01) | |
| *G01N 21/958* | (2006.01) | |
| *H01L 21/67* | (2006.01) | |
| *H01L 27/146* | (2006.01) | |

(52) U.S. Cl.
CPC .......... *G01N 21/01* (2013.01); *G01N 21/958* (2013.01); *G01N 2201/022* (2013.01); *G01N 2201/06113* (2013.01); *H01L 21/67028* (2013.01); *H01L 27/14618* (2013.01)

(58) Field of Classification Search
CPC ......... H01L 27/14618; H01L 27/14625; H01L 2924/0002; H01L 2924/00; H01L 21/67028; G01N 21/01; G01N 21/958; G01N 2201/022; G01N 2201/06113
See application file for complete search history.

(56) References Cited

U.S. PATENT DOCUMENTS

| | | | | |
|---|---|---|---|---|
| 5,498,294 A | * | 3/1996 | Matsushita | ....... H01L 21/67028 134/18 |
| 5,964,954 A | * | 10/1999 | Matsukawa | ............. B08B 1/007 134/18 |
| 6,874,515 B2 | * | 4/2005 | Ishihara | .................... B08B 1/04 134/140 |
| 7,531,816 B2 | * | 5/2009 | Saito | ........................ H01J 37/18 118/719 |
| 9,437,704 B2 | * | 9/2016 | Horii | ....................... C23C 16/06 |
| 9,539,800 B2 | * | 1/2017 | Kito | ................. H01L 21/67092 |
| 2006/0289432 A1 | | 12/2006 | Morita | |
| 2008/0229811 A1 | | 9/2008 | Zhao | |
| 2009/0042324 A1 | | 2/2009 | Son | |
| 2012/0139192 A1 | | 6/2012 | Ooi | |
| 2014/0021332 A1 | * | 1/2014 | Lu | ..................... H01L 27/14618 250/208.1 |

FOREIGN PATENT DOCUMENTS

TW           M493147 U     1/2015

* cited by examiner

*Primary Examiner* — Sang Nguyen

(74) *Attorney, Agent, or Firm* — Winston Hsu

(57) ABSTRACT

A wafer holding apparatus for fixing a wafer having a central portion and a circumference portion includes a holding platform, a lift stage, and a fixing device. The holding platform has a hole structure and a support rib protruding inwardly from an inner wall of the hole structure. The lift stage includes a support platform and a driving arm connected to the support platform for driving the support platform to ascend or descend. When the support platform ascends to a support position to support the wafer, the central portion is flat on the support platform to make the circumference portion flat on a top surface of the support rib in a surface contact manner. The fixing device is for fixing the circumference portion to the top surface of the support rib. After the circumference portion is fixed to the support rib, the lift stage descends to a retracted position.

9 Claims, 6 Drawing Sheets

WAFER HOLDING APPARATUS

BACKGROUND OF THE INVENTION

1. Field of the Invention

The present invention relates to a wafer holding apparatus, and more specifically, to a wafer holding apparatus utilizing a lift stage to support a central portion of a wafer.

2. Description of the Prior Art

In general, the optical property of a glass wafer needs to be measured by a laser measuring device for determining the forming quality of the glass wafer. During the laser measuring process, the glass wafer needs to be placed on a holding platform in advance. The holding platform has a hole structure for allowing the laser beam of the laser measuring device to be incident to the glass wafer, and further has a support rib protruding from an inner wall of the hole structure for supporting the glass wafer. However, since the glass wafer usually has an ultra-thin thickness (e.g. 8" glass wafer with 0.25 mm thickness) and the holding platform only utilizes the support rib with a small width (about 5 mm) to support a circumference portion of the glass wafer, meaning that the hole structure does not provide any support to a central portion of the glass wafer, warpage of the glass wafer occurs accordingly so as to cause an inaccurate measurement result for the warpage region on the glass wafer.

SUMMARY OF THE INVENTION

The present invention provides a wafer holding apparatus for fixing a wafer. The wafer has a central portion and a circumference portion. The wafer holding apparatus includes a holding platform, a lift stage, and a fixing device. The holding platform has a first hole structure and a support rib protruding inwardly from an inner wall of the first hole structure corresponding to the circumference portion for forming a holding space cooperatively with the first hole structure. The lift stage includes a support platform and a driving arm. The driving arm is connected to the support platform for driving the support platform to ascend to a support position or descend to a retracted position out of the first hole structure. When the support platform ascends to the support position to support the wafer placed in the holding space, the central portion of the wafer is flat on the support platform to make the circumference portion of the wafer flat on the top surface of the support rib in a surface contact manner. The fixing device is used for releasably fixing the circumference portion of the wafer to the top surface of the support rib. After the circumference portion of the wafer is fixed to the support rib by the fixing device, the lift stage descends to the retracted position.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
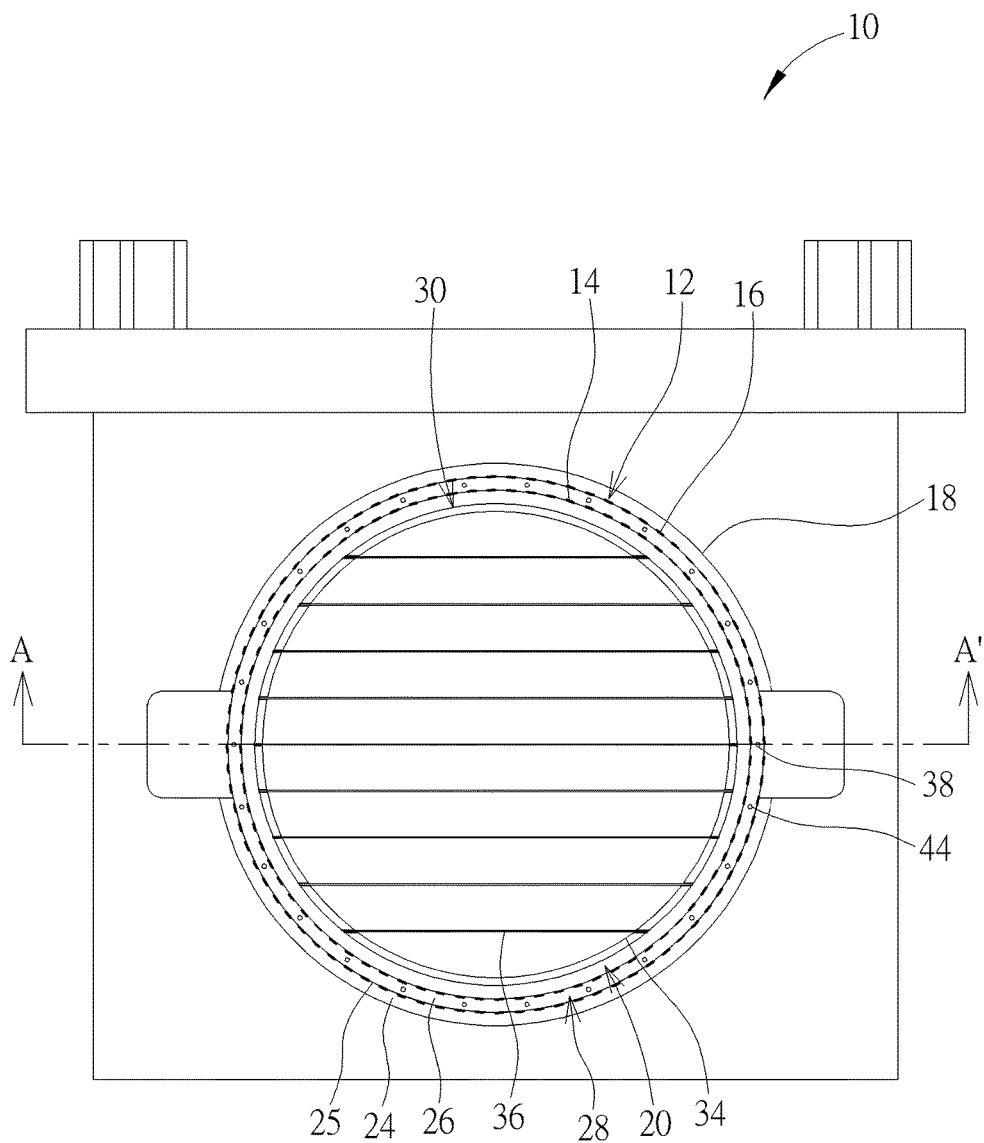
FIG. 1 is a top view of a wafer holding apparatus according to an embodiment of the present invention.
Figure 2:
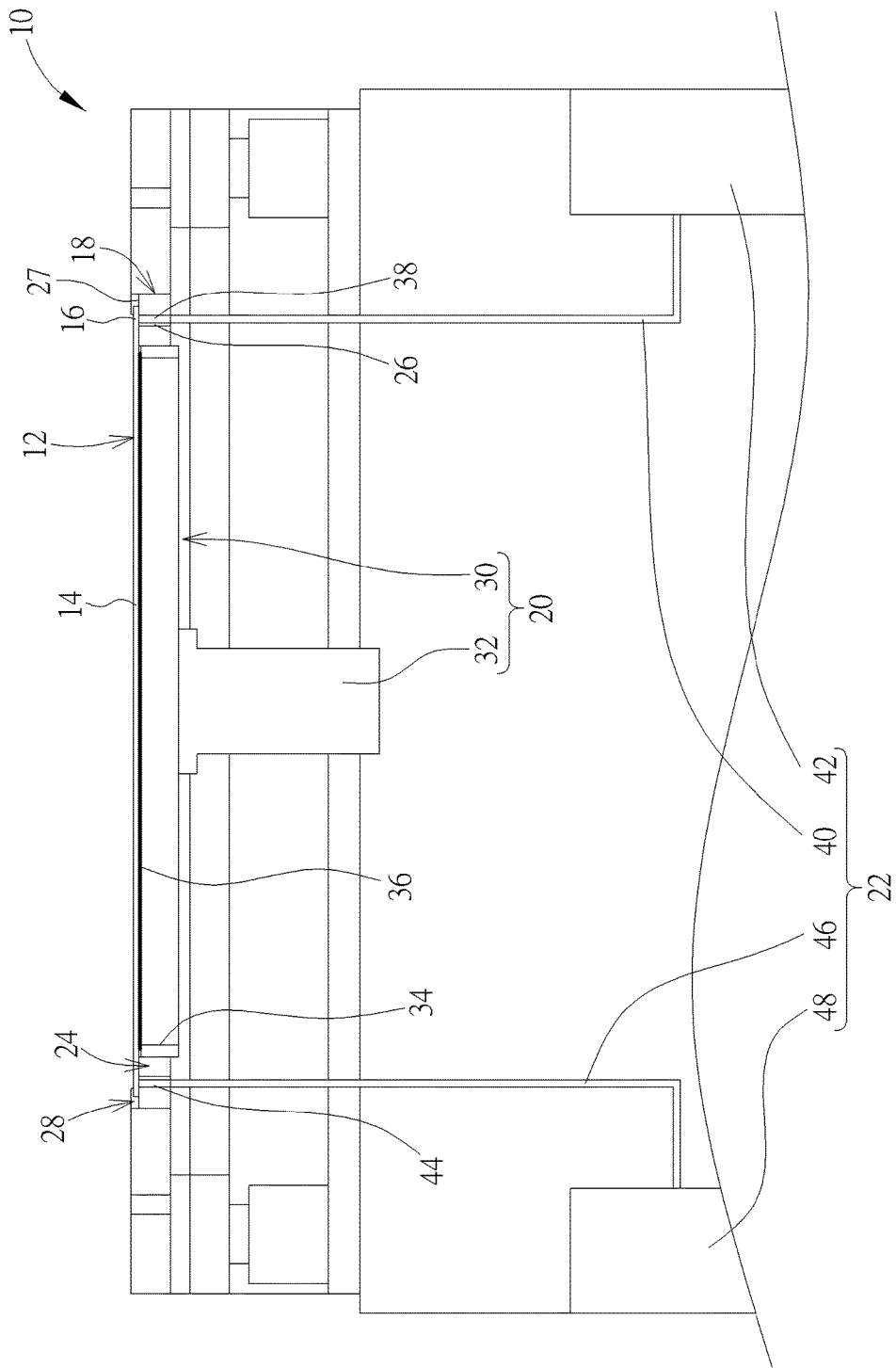
FIG. 2 is a partial cross-sectional diagram of the wafer holding apparatus in FIG. 1 along a cross-sectional line A-A'.

Please refer to FIG. 1 and FIG. 2. FIG. 1 is a top view of a wafer holding apparatus 10 according to an embodiment of the present invention. FIG. 2 is a partial cross-sectional diagram of the wafer holding apparatus 10 in FIG. 1 along a cross-sectional line A-A'. The wafer holding apparatus 10 is used to hold a wafer 12 (e.g. 8" glass wafer with 0.25 mm thickness) for performing the subsequent laser measuring process on the wafer 12 to determine the forming quality of the wafer 12. For clearly showing the design of the wafer holding apparatus 10, the wafer 12 is briefly depicted by dotted lines in FIG. 1. As shown in FIG. 1 and FIG. 2, the wafer 12 has a central portion 14 having a plurality of dies (not shown in figures for simplicity) formed thereon and a circumference portion 16, and the wafer holding apparatus 10 includes a holding platform 18, a lift stage 20, and a fixing device 22. The holding platform 18 has a first hole structure 24 and a support rib 26 protruding inwardly from an inner wall 25 of the first hole structure 24 corresponding to the circumference portion 16 for forming a holding space 28 cooperatively with the first hole structure 24. The lift stage 20 includes a support platform 30 and a driving arm 32. The driving arm 32 is connected to the support platform 30 for driving the support platform 30 (e.g. by motor, pneumatic drive, or hydraulic drive, but not limited thereto) to ascend to support the central portion 14 of the wafer 12 or descend to leave the first hole structure 24.

In this embodiment, the support platform 30 preferably adopts the wire support design for supporting the wafer 12. To be more specific, as shown in FIG. 1, the support platform 30 has a second hole structure 34 and a plurality of wires 36, and two ends of each wire 36 are connected to the second hole structure 34 respectively to make the plurality of wires 36 spaced apart from each other in parallel. Accordingly, when the driving arm 32 drives the support platform 30 to ascend to a support position as shown in FIG. 2, the plurality of wires 36 can cooperatively support the central portion 14 of the wafer 12 placed in the holding space 28 to make the circumference portion 16 of the wafer 12 flat on a top surface 27 of the support rib 26 in a surface contact manner. In practical application, tension of each wire 36 could be adjusted preferably by a wire tightening tool (but not limited thereto) to ensure that each wire 36 can be coplanar with the top surface 27 of the support rib 26. To be noted, in this embodiment, a laser distance meter could preferably be utilized to determine whether each wire 36 is coplanar with the top surface 27. For example, if it is determined that there is one wire 36 loose and not coplanar with the top surface 27, the wire tightening tool could be utilized to tighten this loose wire 36. The related description for the aforesaid wire tightening design is omitted herein since it is commonly seen in the prior art.

As for the fixing design of the fixing device 22, it is as shown in FIG. 2. The fixing device 22 is used for releasably fixing the circumference portion 16 of the wafer 12 to the top surface 27 of the support rib 26. As shown in FIG. 2, the holding platform 18 could further have a plurality of first vacuum holes 38 formed on the support rib 26, and the fixing device 22 could include a first vacuum line 40 and a first vacuum pump 42. The first vacuum line 40 is connected to the plurality of first vacuum holes 38 and the first vacuum pump 42. Accordingly, the first vacuum pump 42 could vacuum the plurality of first vacuum holes 38 via the first vacuum line 40 to absorb the circumference portion 16 of the wafer 12 on the top surface 27 of the support rib 26. Moreover, in practical application, the holding platform 18 could further have a plurality of second vacuum holes 44 formed on the support rib 26, and the fixing device 22 could further include a second vacuum line 46 and a second vacuum pump 48. The second vacuum line 46 is connected to the plurality of second vacuum holes 44 and the second vacuum pump 48, so that the second vacuum pump 48 could vacuum the plurality of second vacuum holes 44 via the second vacuum line 46 to absorb the circumference portion 16 of the wafer 12 on the top surface 27 of the support rib 26. In this embodiment, the plurality of first vacuum holes 38 and the plurality of second vacuum holes 44 are alternately formed on the support rib 26 in a radial arrangement, but not limited thereto. In such a manner, even if vacuum between the wafer 12 and one of the first vacuum pump 42 and the second vacuum pump 48 is lost, the fixing device 22 could still absorb the circumference portion 16 of the wafer 12 on the support rib 26 via vacuum between the wafer 12 and the other one of the first vacuum pump 42 and the second vacuum pump 48.

Figure 3:
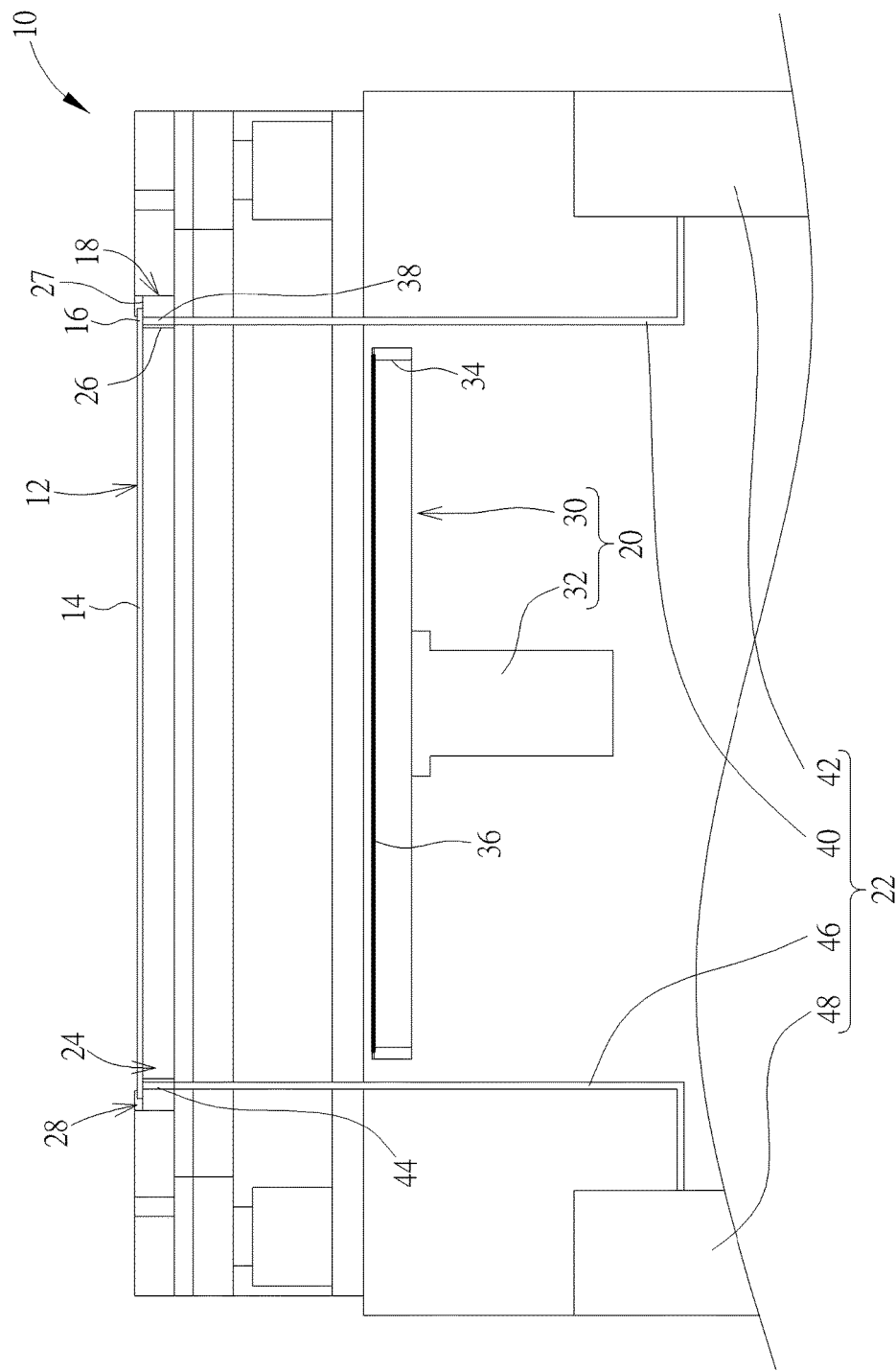
FIG. 3 is a cross-sectional diagram of a driving arm in FIG. 2 driving a support platform to descend to a retracted position.

More detailed description for the wafer holding operation of the wafer holding apparatus 10 is provided as follows. Please refer to FIG. 1, FIG. 2, and FIG. 3. FIG. 3 is a cross-sectional diagram of the driving arm 32 in FIG. 2 driving the support platform 30 to descend to a retracted position. When a user wants to place the wafer 12 on the wafer holding apparatus 10 for determining the forming quality of the wafer 12, the driving arm 32 drives the support platform 30 to ascend to the support position as shown in FIG. 2 first for making the plurality of wires 36 coplanar with the top surface 27 of the support rib 26. Subsequently, the user could place the wafer 12 in the holding place 28, so that the central portion 14 of the wafer 12 can be flat on the plurality of wires 36 to make the circumference portion 16 of the wafer 12 flat on the top surface 27 of the support rib 26 in a surface contact manner.

After the wafer 12 is supported by the lift stage 20 and the support rib 26, the fixing device 22 could utilize the first vacuum pump 42 to vacuum the plurality of first vacuum holes 38 via the first vacuum line 40 and utilize the second vacuum pump 48 to vacuum the plurality of second vacuum holes 44 via the second vacuum line 46 to absorb the circumference portion 16 of the wafer 12 on the top surface 27 of the support rib 26, so as to fix the wafer 12 flatly in the holding space 28. Finally, after the circumference portion 16 of the wafer 12 is fixed to the support rib 26 by the fixing device 22, the driving arm 32 could drive the lift stage 28 to descend to the retracted position to leave the first hole structure 24 as shown in FIG. 3. In such a manner, the holding platform 18 could move to a next position where the wafer 12 could be measured by a laser measuring device through the first hole structure 24 in the condition that the wafer 12 is flatly fixed in the holding space 28 with no warpage, so as to solve the prior art problem that warpage of the glass wafer causes the laser measuring device to generate an inaccurate measurement result. Furthermore, since the wafer 12 is fixed in the holding space 28 securely, the measurement result for the forming quality of the wafer 12 can be more precise.

On the other hand, after the aforesaid laser measuring process is completed, vacuum between the wafer 12 and the first vacuum pump 42 and vacuum between the wafer 12 and the second vacuum pump 48 could be released accordingly for the user to take the wafer 12 out of the wafer holding apparatus 10 conveniently.

Figure 4:
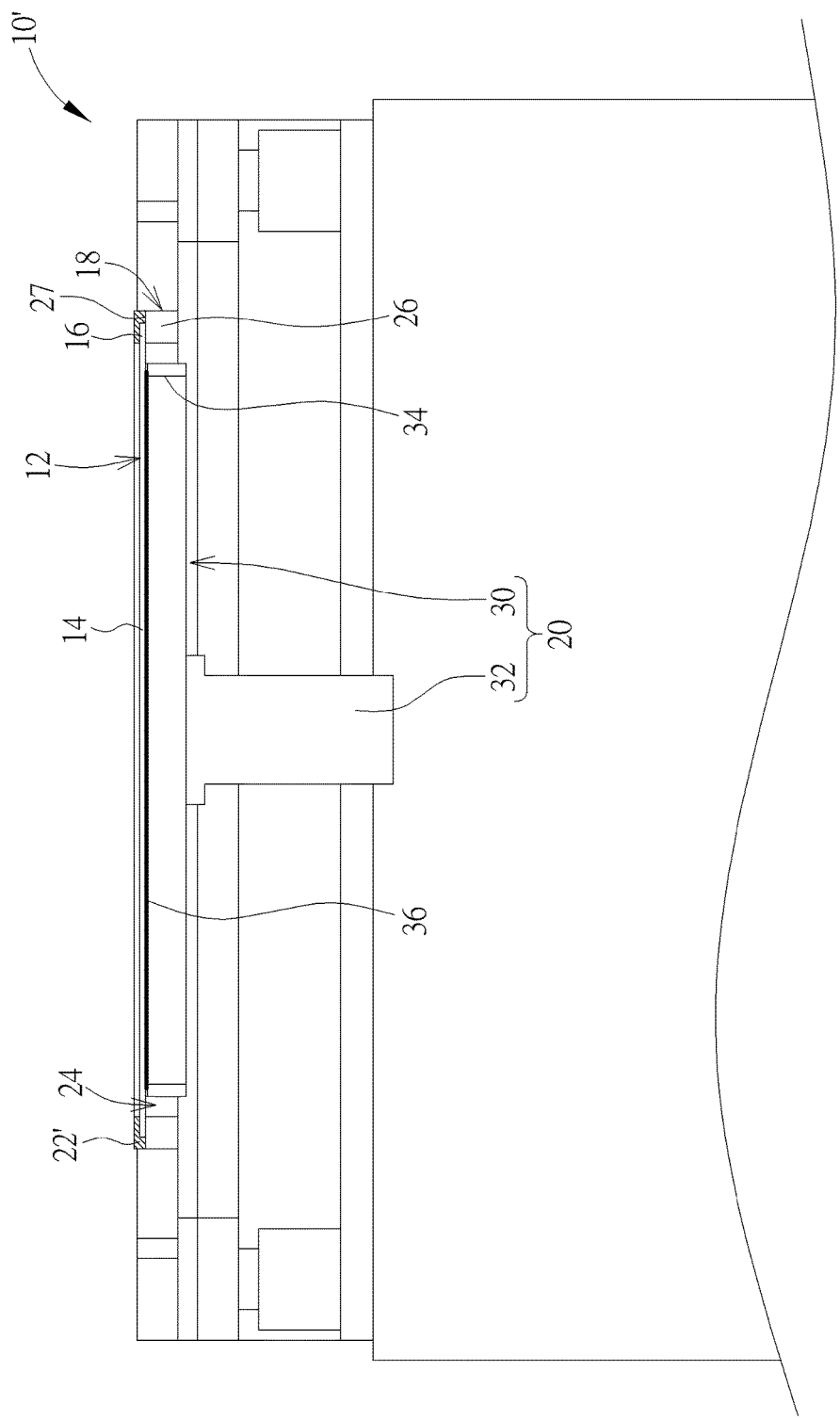
FIG. 4 is a partial cross-sectional diagram of a wafer holding apparatus according to another embodiment of the present invention.

The design of the fixing device is not limited to the aforesaid embodiment, meaning that the present invention could adopt other design for releasably fixing the wafer to the support rib. For example, please refer to FIG. 4, which is a partial cross-sectional diagram of a wafer holding apparatus 10' according to another embodiment of the present invention. Components both mentioned in this embodiment and the aforesaid embodiment represent components with similar structures or functions, and the related description is omitted herein. As shown in FIG. 4, the wafer holding apparatus 10' includes the holding platform 18, the lift stage 20, and a fixing device 22'. In this embodiment, the fixing device 22' is a fixing ring. Accordingly, when the circumference portion 16 of the wafer 12 is flat on the top surface 27 of the support rib 26 as mentioned above, the fixing device 22' could be detachably staked on the circumference portion 16 of the wafer 12 to press the circumference portion 16 of the wafer 12 on the top surface 27 of the support rib 26, so as to make the wafer 12 flatly fixed on the support rib 26 for the subsequent laser measuring process.

Figure 5:
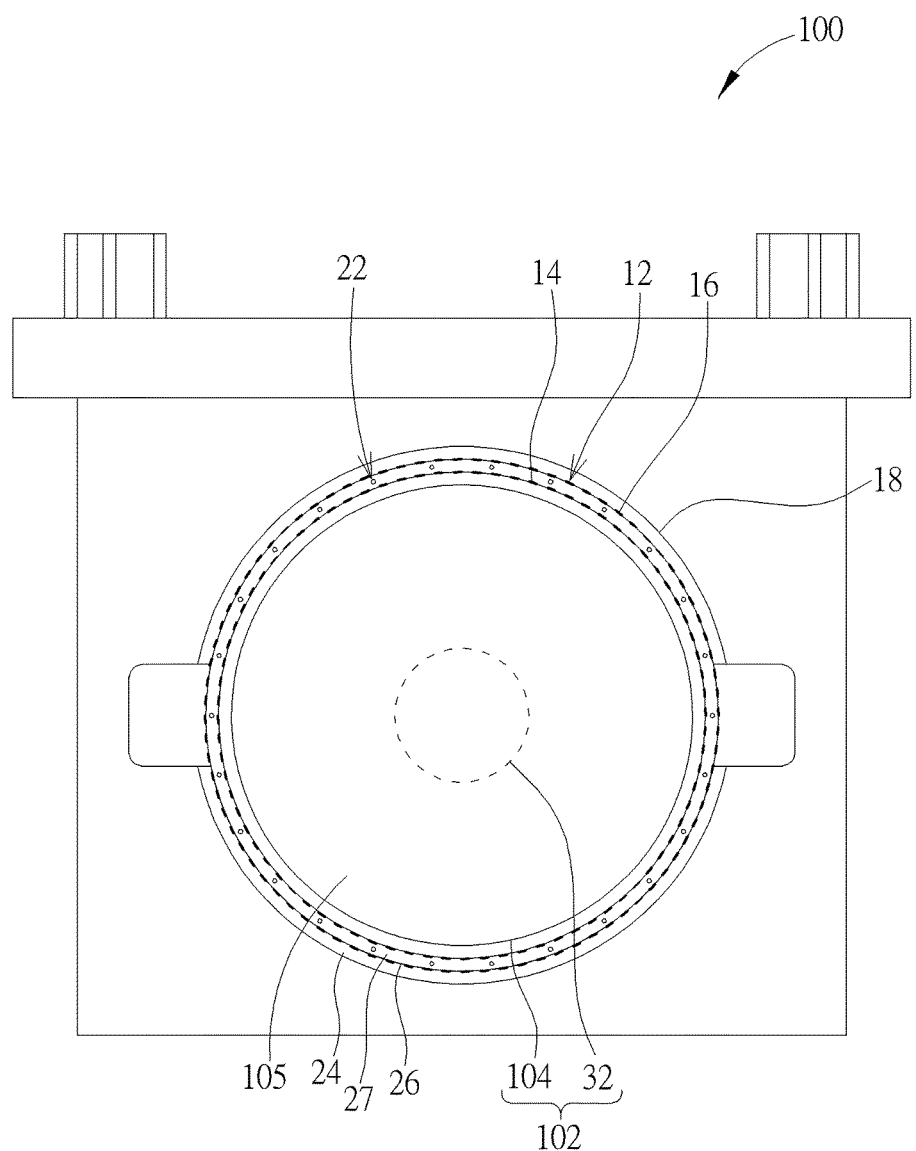
FIG. 5 is a top view of a wafer holding apparatus according to another embodiment of the present invention.

It should be mentioned that the support design of the support platform is not limited to the aforesaid embodiments in which the wafer is supported by the wires in a linear contact manner. That is to say, in another embodiment, the present invention could adopt other support design for supporting the wafer. For example, please refer to FIG. 5, which is a top view of a wafer holding apparatus 100 according to another embodiment of the present invention. Components both mentioned in this embodiment and the aforesaid embodiments represent components with similar structures or functions, and the related description is omitted herein. As shown in FIG. 5, the wafer holding apparatus 100 includes the holding platform 18, the fixing device 22, and a lift stage 102. In this embodiment, the lift stage 102 includes a support platform 104 and the driving arm 32 (briefly depicted by dotted lines in FIG. 5), and the support platform 104 has a support surface 105. The driving arm 32 is connected to the support platform 104 for driving the support platform 104 to ascend to the support position to make the support surface 105 coplanar with the top surface 27 of the support rib 26. Accordingly, when the user places the wafer 12 on the wafer holding apparatus 100, the central portion 14 of the wafer 12 can be flat on the support surface 105 of the support platform 104 in a surface contact manner to make the circumference portion 16 of the wafer 12 flat on the top surface 27 of the support rib 26. As for the other related description for the wafer holding apparatus 100 (e.g. the wafer fixing design, the wafer holding operation), it could be reasoned by analogy according to the aforesaid embodiments and omitted herein.

Figure 6:
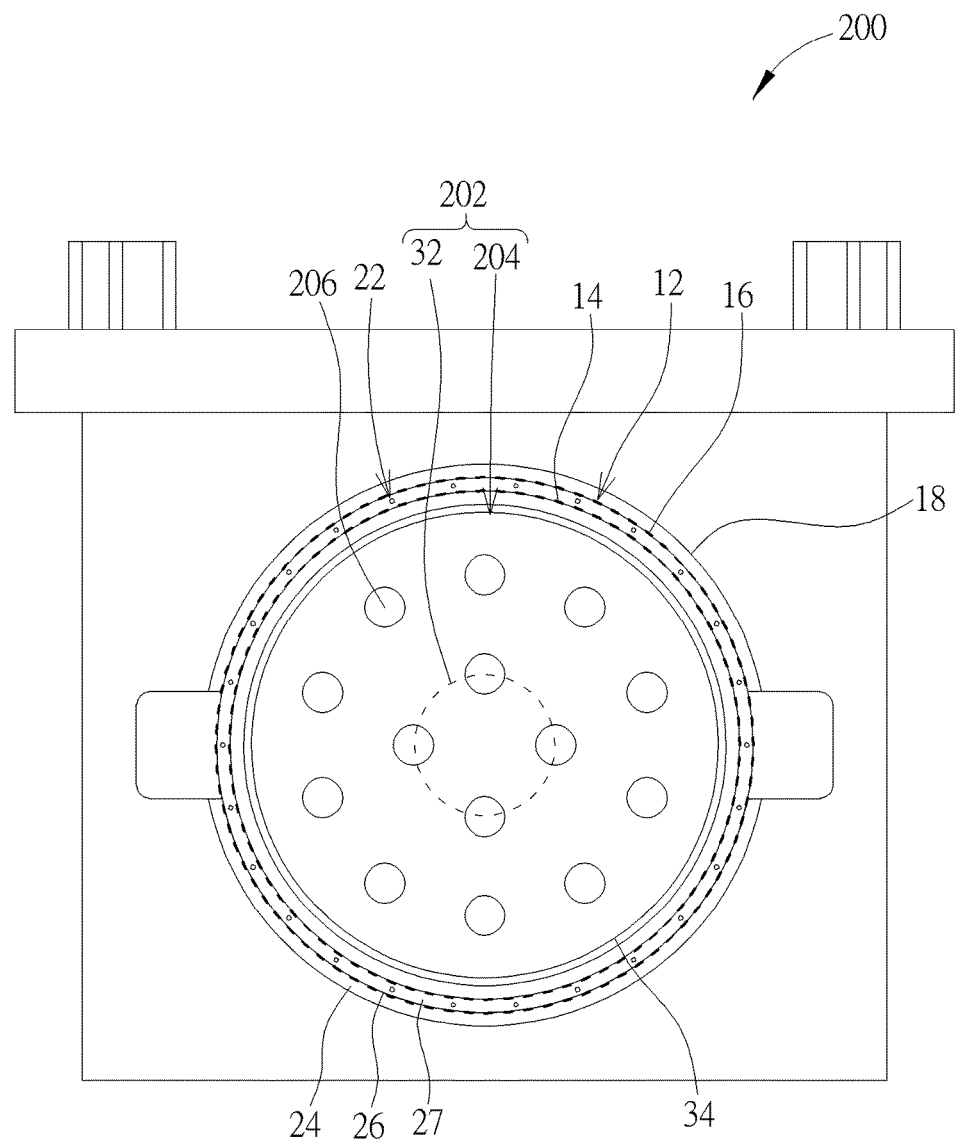
FIG. 6 is a top view of a wafer holding apparatus according to another embodiment of the present invention.

Furthermore, please refer to FIG. 6, which is a top view of a wafer holding apparatus 200 according to another embodiment of the present invention. Components both mentioned in this embodiment and the aforesaid embodiment represent components with similar structures or functions, and the related description is omitted herein. As shown in FIG. 6, the wafer holding apparatus 200 includes the holding platform 18, the fixing device 22, and a lift stage 202. In this embodiment, the lift stage 202 includes the driving arm 32 (briefly depicted by dotted lines in FIG. 6) and a support platform 204, and the support platform 204 has the second hole structure 34 and a plurality of support pins 206. The plurality of support pins 206 is movably disposed in the second hole structure 34, so that each support pin 206 could be driven (e.g. by motor, pneumatic drive, or hydraulic drive, but not limited thereto) to support the central portion 14 of the wafer 12 cooperatively. Accordingly, when the driving arm 32 drives the support platform 204 to ascend to the support position as shown in FIG. 6, each support pin 206 can cooperatively support the central portion 14 of the wafer 12 to make the circumference portion 16 of the wafer 12 flat on the top surface 27 of the support rib 26 in a surface contact manner. As for the other related description for the wafer holding apparatus 200 (e.g. the wafer fixing design, the wafer holding operation), it could be reasoned by analogy according to the aforesaid embodiments and omitted herein.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A wafer holding apparatus for fixing a wafer, the wafer having a central portion and a circumference portion, the wafer holding apparatus comprising:
   a holding platform having a first hole structure and a support rib protruding inwardly from an inner wall of the first hole structure corresponding to the circumference portion for forming a holding space cooperatively with the first hole structure to support the wafer in the first hole structure via the holding space;
   a lift stage comprising:
      a support platform retractably disposed through the first hole structure; and
      a driving arm connected to the support platform for driving the support platform to ascend to a support position in the first hole structure or descend to a retracted position out of the first hole structure, the central portion of the wafer in the first hole structure being flat on the support platform to make the circumference portion of the wafer flat on a top surface of the support rib in a surface contact manner when the support platform ascends to the support position to support the wafer placed in the holding space; and
   a fixing device for releasably fixing the circumference portion of the wafer to the top surface of the support rib to fix the wafer on the holding platform when the support rib supports the wafer in the first hole structure;
   wherein after the circumference portion of the wafer is fixed to the support rib by the fixing device, the lift stage descends to the retracted position.

2. The wafer holding apparatus of claim 1, wherein the holding platform further has a plurality of first vacuum holes formed on the support rib, the fixing device comprises a first vacuum line and a first vacuum pump, the first vacuum line is connected to the plurality of first vacuum holes and the first vacuum pump, and the first vacuum pump vacuums the plurality of first vacuum holes via the first vacuum line to absorb the circumference portion of the wafer on the top surface of the support rib.

3. The wafer holding apparatus of claim 2, wherein the holding platform further has a plurality of second vacuum holes formed on the support rib, the fixing device further comprises a second vacuum line and a second vacuum pump, the second vacuum line is connected to the plurality of second vacuum holes and the second vacuum pump, and the second vacuum pump vacuums the plurality of second vacuum holes via the second vacuum line to absorb the circumference portion of the wafer on the top surface of the support rib.

4. The wafer holding apparatus of claim 3, wherein the plurality of first vacuum holes and the plurality of second vacuum holes are alternately formed on the support rib in a radial arrangement.

5. The wafer holding apparatus of claim 1, wherein the support platform has a second hole structure and a plurality of wires, and two ends of each wire are connected to the second hole structure respectively to make the plurality of wires spaced apart from each other in parallel for supporting the central portion of the wafer to make the circumference portion of the wafer flat on the top surface of the support rib.

6. The wafer holding apparatus of claim 5, wherein tension of each wire is selectively adjusted by a wire tightening tool to make the plurality of wires coplanar with the top surface of the support rib.

7. The wafer holding apparatus of claim 1, wherein the fixing device comprises a fixing ring, and when the circumference portion of the wafer is flat on the top surface of the support rib, the fixing ring is detachably staked on the circumference portion of the wafer to press the circumference portion of the wafer on the top surface of the support rib.

8. The wafer holding apparatus of claim 1, wherein the support platform has a support surface, and the driving arm drives the support platform to ascend to the support position to make the support surface of the support platform coplanar with the top surface of the support rib.

9. The wafer holding apparatus of claim 1, wherein the support platform has a second hole structure and a plurality of support pins, and the support pins are movably disposed in the second hole structure for supporting the central portion of the wafer cooperatively to make the circumference portion of the wafer flat on the top surface of the support rib.

* * * * *